United States Patent [19]
Rutenberg

[11] Patent Number: 4,965,725
[45] Date of Patent: Oct. 23, 1990

[54] NEURAL NETWORK BASED AUTOMATED CYTOLOGICAL SPECIMEN CLASSIFICATION SYSTEM AND METHOD

[75] Inventor: Mark R. Rutenberg, Monsey, N.Y.

[73] Assignee: Nueromedical Systems, Inc., Monsey, N.Y.

[21] Appl. No.: 179,060

[22] Filed: Apr. 8, 1988

[51] Int. Cl.⁵ .................. G06F 15/18; G06F 15/42; G06F 15/70; G06K 9/62
[52] U.S. Cl. .................. 364/413.1; 382/15; 382/36
[58] Field of Search .............. 382/15, 36; 364/513, 364/801, 807, 200 MS File, 900 MS File, 413.1; 307/201

[56] References Cited

U.S. PATENT DOCUMENTS

| | | | |
|---|---|---|---|
| 4,000,417 | 12/1976 | Adkisson et al. | 250/201 |
| 4,591,980 | 5/1986 | Huberman et al. | 364/200 |
| 4,700,298 | 10/1987 | Palcic et al. | 364/413.1 |
| 4,805,225 | 2/1989 | Clark | 382/15 |

OTHER PUBLICATIONS

Minsky, M. L. et al., "Perceptrons", (Expanded Edition), The MIT Press, Cambridge, Mass., 1988.
Rumelhart, D. E. et al., "Parallel Distributed Processing", vol. 1: Foundations, The MIT Press, Cambridge, Mass., 1986.
Pao, Y., "Adaptive Pattern Recognition and Neural Networks", Addison-Wesley Publishing Company, Inc., 1989.
Fukushima, K., "Neural Network Model for Selective Associative Recall", Applied Optics, vol. 26, No. 23, Dec. 1987, 4985-4992.
"Automation of Uterine Cervical Cytology: Accomplishments and Goals" Dorothy L. Rosenthal, M. D., Univ. of Calif., 1986 Elsevier Science Publishers, 65-72.
"Biology of Disease: Application of Quantitative Microscopy in Tumer Pathology" Hall and Fu, Univ. of Calif. Laboratory Investigation; vol. 53, No. 1, 1985, 5-21.
"Microcomputer-Based Image Processing Workstations for Cytology," Thomas Hall, Darius Keyani, Dorothy Rosenthal; Applied Optics, vol. 26, No. 16, Aug. 15, 1987 pp. 3266-3269.
"Automated Cervical Smear Classification," D. Tien, P. Nickolls, W. Liew, A. Yeung, Y. C. Liang, J. Tucker; IEEE/Ninth Annual Conference of the Engineering in Medicine and Biology Society, 1987, 1457-8.
"Neurocomputing: Picking the Human Brain," Robert Hecht-Nielsen, IEEE Spectrum, Mar. 1988, 36-41.
"An Introduction to Computing with Neural Nets" Richard P. Lippmann IEEE ASSP Magazine, Apr. 1987, 4-22.
Oud, P. S. et al., "Sample Preparation in Diagnostic Cytology: Present Status and New Developments", Diagnostics & Clinical Testing, vol. 28, No. 3, Mar. 1990, 16-19.
Coleman, D. V., et al., "Clinical Cytotechnology", Butterworth & Co., Ltd., 1989, Chapter 25: Automation by K. C. Watts and O. A. N. Husain, 441-454.
Koss, L. G., "Diagnostic Cytology and Its Histopathologic Bases", J. B. Lippincott Company, Philadelphia, 1979, 1152-3.
Rennie, J. "Cancer Catcher: Neural Net Catches Errors that Slip Through Pap Tests", Scientific American, May 1990, (Page Unknown, Reprint).
Tanaka, N. et al., "CYBEST Model 3 Automated Cytologic Screening System for Uterine Cancer Utilizing Image Analysis Processing", Analytical and Quantitative Cytology, vol. 4, No. 4, Dec. 1982, 279-285.
ANSim TM User's Manual, Version 2.02, Science Applications International Corp. (SAIC), San Diego,

(List continued on next page.)

Primary Examiner—Clark A. Jablon
Attorney, Agent, or Firm—Renner, Otto, Boisselle & Sklar

[57] ABSTRACT

An automated screening system and method for cytological specimen classification in which a neural network is utilized in performance of the classification function. Also included is an automated microscope and associated image processing circuitry.

43 Claims, 5 Drawing Sheets

OTHER PUBLICATIONS

Calif., pp. 4-13-18, 6-13-15, 7-3-7, 8-8-10, no date given.

Imasato, Y. et al., "CYBEST-AUTOMATED PAP SMEAR PRESCREENER", Toshiba Review, (International Edition) No. 100, Nov.-Dec. 1975, 60-63.

Rosenthal, D. "Critical Review of Potential Neural Nets in Diagnostic Pathology", XII International Meeting of the Society for Analytical Cytology, Breckenridge, Colo., Sep. 1988, 4 pp.

Egbert, D. D. et al., "Preprocessing of Biomedical Images for Neurocomputer Analysis", IEEE International Conference on Neural Networks, San Diego, Calif., Jul. 1988, vol. 1, pp. 561-58.

Dayhoff, R. E. et al., "Segmentation of True Color Microscopic Images Using a Back Propagation Neural Network", Neural Networks, vol. 1, No. 1, Suppl. 1988, 169.

Oldham, W. J. B. et al., "Neural Network Recognition of Mammographic Lesions", 73rd Scientific Assembly and Annual Meeting of the Radiological Society of North America, Nov. 1987.

Fukushima, K. "Self-Organizing Neural Network Models for Visual Pattern Recognition", Acta Neurochir Suppl. (Wein), vol. 41, 1987, 51-67.

NEURAL NETWORK BASED AUTOMATED CYTOLOGICAL SPECIMEN CLASSIFICATION SYSTEM AND METHOD

TECHNICAL FIELD

This invention relates generally, as indicated, to cell classification and, more particularly, to the use of neural networks and/or neurocomputers for increasing the speed and accuracy of cell classification.

BACKGROUND OF THE INVENTION

The cervical smear (Pap test) is the only mass screening cytological examination which requires visual inspection of virtually every cell on the slide. The test suffers from a high false negative rate due to the tedium and fatigue associated with its current manual mode of performance. Cell classification is typically performed on a "piece-work" basis by "cytotechnicians" employed by pathology laboratories and in some circumstances by salaried technicians. Due to the clearly life threatening nature of the false negative problem with its resultant possibility of undiagnosed cervical cancer, the American Cancer Society is considering doubling the frequency of recommended Pap smears. This, however, will certainly overload an already overburdened cervical screening industry as increasingly fewer individuals are willing to enter the tedious and stressful field of manual cervical smear classification. An American Cancer Society recommendation to increase Pap smear frequency may only serve to increase the false negative rate by decreasing the amount of time spent on manual examination of each slide. A thorough manual examination should take no less than fifteen minutes per slide although a cytotechnician, especially one under a heavy workload, may spend less than half this amount of time. The College of American Pathology is well aware of this problem and would rapidly embrace an automated solution to cervical smear screening.

Due to the clear commercial potential for automated cervical smear analysis several attempts to this end have been made in the prior art. These attempts have proven to be unsuccessful since they have relied exclusively on classical pattern recognition technology (geometric, syntactic, template, statistical) or artificial intelligence (AI) based pattern recognition, i.e., rule-based expert systems. There is, however, no clear algorithm or complete and explicit set of rules by which the human cytotechnician or pathologist uses his experience to combine a multitude of features to make a classification in gestalt manner. Cervical smear classification is, therefore, an excellent application for neural network based pattern recognition.

An example of the limitations of the prior art can be found in the 1987 reference entitled "Automated Cervical Screen Classification" by Tien et al, identified further below.

Background references of interest are, as follows:

Rumelhart, David E. and McClelland, James L., "Parallel Distributed Processing," MIT Press, 1986, Volume 1;

Tien, D. et al, "Automated Cervical Smear Classification," Proceedings of the IEEE/Ninth Annual Conference of the Engineering in Medicine and Biology Society, 1987, p. 1457–1458;

Hecht-Nielsen, Robert, "Neurocomputing: Picking the Human Brain," IEEE Spectrum, March, 1988, p. 36–41; and Lippmann, Richard P., "An Introduction to Computing with Neural Nets," IEEE ASSP Magazine, April, 1987, p. 4–22.

BRIEF SUMMARY OF THE INVENTION

It is, therefore, a principal object of the present invention to provide an automated system and method for the classification of cytological specimens into categories, for example, categories of diagnostic significance.

Briefly, the invention includes an initial classifier (sometimes referred to as a primary classifier) preliminarily to classify a cytological specimen and a subsequent classifier (sometimes referred to as a secondary classifier) to classify those portions of the cytological specimen selected by the initial classifier for subsequent classification, wherein the subsequent classifier includes a neural computer or neural network.

In one embodiment the primary classifier may include a commercially available automated microscope in the form of a standard cytology microscope with a video camera or CCD array with the microscope stage controlled for automatic scanning of a slide. Images from the camera are digitized and outputted to the secondary classifier in the form of a computer system. The computer system includes a neural network as defined below and is disclosed, too, in several of the references referred to herein, which is utilized in the performance of cell image identification and classification into groups of diagnostic interest. In an alternate embodiment the primary classifier may include a neural network. Other alternate embodiments also are disclosed below.

It is a further object of the present invention that it perform its classification of a group of specimens within the period of time typically consumed for this task by careful manual screening (i.e., approximately 15 minutes/specimen).

It is a further object of the present invention that it perform its classification on cytological specimens which contain the numbers and types of objects other than single layers of cells of interest that are typically found in cervical smears (e.g., clumps of cells, overlapping cells, debris, leucocytes, bacteria, mucus).

It is a further object of the present invention to perform the above-described classification on cervical smears for the detection of pre-malignant and malignant cells.

It is a further object of the present invention that it perform its classification with smaller false negative error rates than typically found in conventional manual cervical smear screening.

An advantage of the cytological classification system of the present invention is that classification of cytological specimens into medically significant diagnostic categories will be more reliable, i.e., with lower false negative error rates.

A further advantage of the cytological classification system of the present invention is that it does not require a modification in the procedure by which cellular specimens are obtained from the patient.

A further advantage of the cytological classification system of the present invention is that it will permit reliable classification within processing time constraints that permit economically viable operation.

These and other objects, advantages and features of the present invention will become evident to those of ordinary skill in the art after having read the following detailed description of the preferred embodiment.

It is noted here that the published articles cited herein are specifically incorporated by reference.

Moreover, it is noted here that the invention is described herein mainly with respect to classification of cytological specimens in the form of a cervical smear, e.g., as typically is done in connection with a Pap test. However, it will be appreciated that this is but one example of the application of the principles of the invention which are intended for application for classification of many other cytological specimens.

DESCRIPTION OF THE PREFERRED AND ALTERNATE EMBODIMENTS

Figure 1:
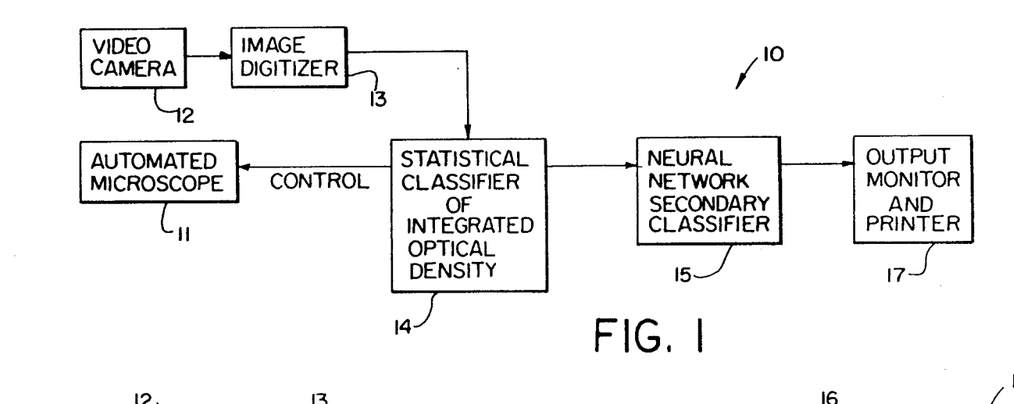
FIG. 1 is a block diagram for a neural network based automated cytological specimen screening device in accordance with the present invention.

FIG. 1 illustrates a neural network based automated cytological specimen screening device in accordance with the present invention and referred to by the general reference numeral 10. The classification device 10 includes an automated microscope 11, a video camera or CCD device 12, an image digitizer 13, and classifier stages 14, and 15.

The automated microscope 11 effects relative movement of the microscope objective and the specimen, and video camera or CCD 12 obtains an image or picture of a specific portion of the cytological specimen. The image is digitized by the image digitizer 13 and the information therefrom is coupled to the classifier 14. In the preferred embodiment, classifier 14 is a commercially available statistical classifier which identifies cell nuclei of interest by measurement of their integrated optical density (nuclear stain density). This is the sum of the pixel grey values for the object, corrected for optical errors. Compared to normal cells, malignant cells tend to possess a larger, more densely staining nucleus.

Objects which pass classifier 14 consist of pre-malignant and malignant cells but also include other objects with high integrated optical density such as cell clumps, debris, leucocytes and mucus. The task of the secondary classifier 15 is to distinguish pre-malignant and malignant cells from these other objects.

A neural network is utilized to implement secondary classifier 15. Detailed descriptions of the design and operation of neural networks suitable for implementation of secondary classifier 15 can be found in the references cited herein. A brief description of this information is provided below.

Based on the data obtained by the primary classifier for the cytological specimen, the secondary classifier is used to check specific areas of the specimen that are, for example, determined to require further screening or classification. Such further examination by the secondary classifier may be effected by reliance on the already obtained digitized image data for the selected areas of the specimen or by the taking of additional data by the components 11-13 or by other commercially available optical or other equipment that would provide acceptable data for use and analysis by the secondary classifier 15.

A neural network is a highly parallel distributed system with the topology of a directed graph. The nodes in neural networks are usually referred to as "processing elements" or "neurons" while the links are generally known as "interconnects." Each processing element accepts multiple inputs and generates a single output signal which branches into multiple copies that are in turn distributed to the other processing elements as input signals. Information is stored in the strength of the connections known as weights. In an asynchronous fashion, each processing element computes the sum of products of the weight of each input line multiplied by the signal level (usually 0 or 1) on that input line. If the sum of products exceeds a preset activation threshold, the output of the processing element is set to 1, if less, it is set to 0. Learning is achieved through adjustment of the values of the weights.

For the present invention, the preferred embodiment is achieved by utilization of a three-layer neural network of the type described in the Lippman reference as a "multi-layer perception" and discussed in detail in Chapter 8 of the Rumelhart reference. Other types of neural network systems also may be used.

Figure 2:
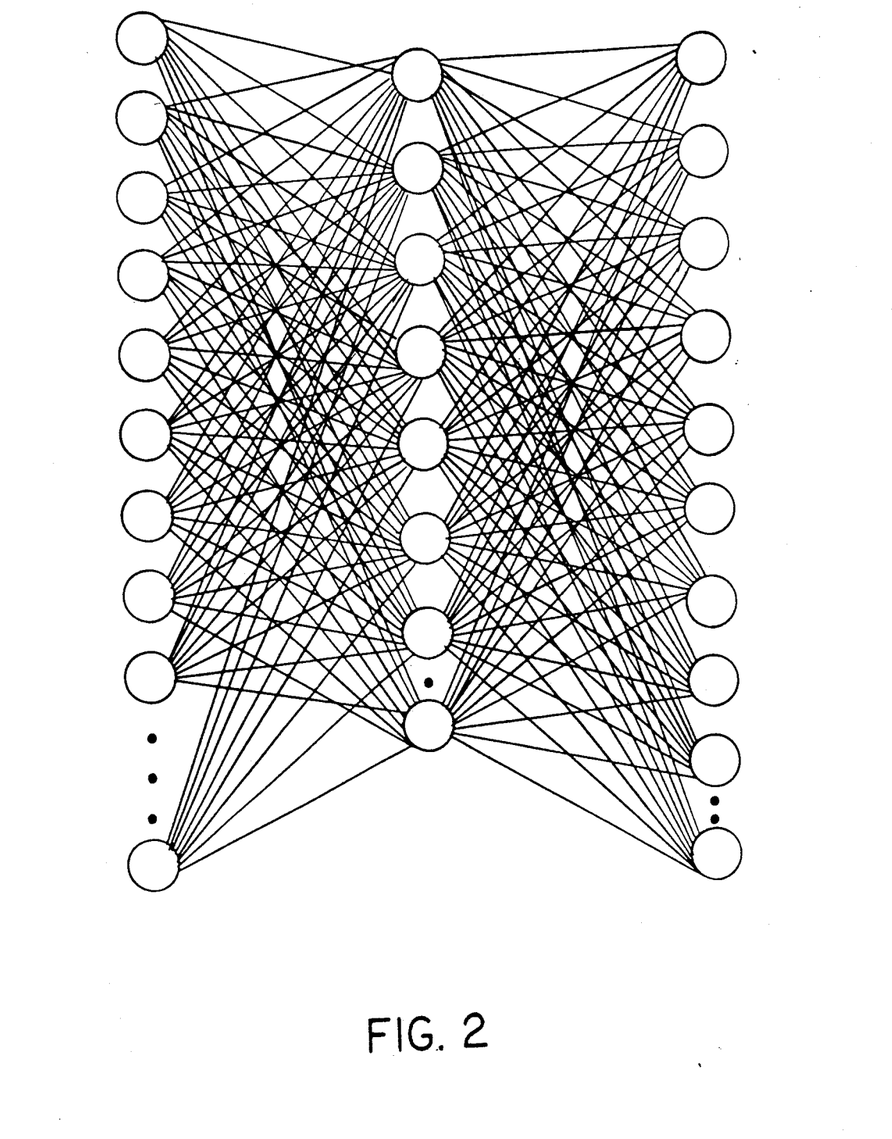
FIG. 2 is a representation of a three-layer neural network of the type utilized in the preferred embodiment.

A three-layer neural network consists of an input layer, an output layer, and an intermediate hidden layer. The intermediate layer is required to allow for internal representation of patterns within the network. As shown by Minsky and Papert in their 196 book entitled "Perceptrons" (MIT Press), simple two-layer associative networks are limited in the types of problems they can solve. A two-layer network with only "input" and "output" processing elements can only represent mappings in which similar input patterns lead to similar output patterns. Whenever the real world problem is not of this type, a three-layer network is required. It has been shown that with a large enough hidden layer, a threelayer neural network can always find a representation that will map any input pattern to any desired output pattern. A generic three-layer neural network of the type utilized in the preferred embodiment is shown in FIG. 2.

Several important features of neural network architectures distinguish them from prior art approaches to the implementation of classifier 15.

1. There is little or no executive function. There are only very simple units each performing its sum of products calculation. Each processing element's task is thus limited to receiving the inputs from its neighbors and, as a function of these inputs, computing an output value which it sends to its neighbors. Each processing element performs this calculation periodically, in parallel with, but not synchronized to, the activities of any of its neighbors.

2. All knowledge is in the connections. Only very short term storage can occur in the states of the processing elements. All long term storage is represented by the values of the connection strengths or "weights" between the processing elements. It is the rules that establish these weights and modify them for learning that primarily distinguish one neural network model from another. All knowledge is thus implicitly represented in the strengths of the connection weights rather than explicitly represented in the states of the processing elements.

3. In contrast to algorithmic computers and expert systems, the goal of neural net learning is not the formulation of an algorithm or a set of explicit rules. During learning, a neural network self-organizes to establish the global set of weights which will result in its output for a given input most closely corresponding to what it is told is the correct output for that input. It is this adaptive acquisition of connection strengths that allows a neural network to behave as if it knew the rules. Conventional computers excell in applications where the knowledge can be readily represented in an explicit algorithm or an explicit and complete set of rules. Where this is not the case, conventional computers encounter great difficulty. While conventional computers can execute an algorithm much more rapidly than any human, they are challenged to match human performance in non-algorithmic tasks such as pattern recognition, nearest neighbor classification, and arriving at the optimum solution when faced with multiple simultaneous constraints. If N exemplar patterns are to be searched in order to classify an unknown input pattern, an algorithmic system can accomplish this task in approximately order N time. In a neural network, all of the candidate signatures are simultaneously represented by the global set of connection weights of the entire system. A neural network thus automatically arrives at the nearest neighbor to the ambiguous input in order 1 time as opposed to order N time.

For the present invention, the preferred embodiment is achieved by utilization of a three-layer backpropagation network as described in the Rumelhart reference for the neural network of classifier stage 15. Backpropagation is described in detail in the Rumelhart reference. Briefly described, it operates as follows. During net training, errors (i.e., the difference between the appropriate output for an exemplar input and the current net output for that output) are propagated backwards from the output layer to the middle layer and then to the input layer. These errors are utilized at each layer by the training algorithm to readjust the interconnection weights so that a future presentation of the exemplar pattern will result in the appropriate output category. Following the net training, during the feed-forward mode, unknown input patterns are classified by the neural network into the exemplar category which most closely resembles it.

The output of neural net classifier 15 indicates the presence or absence of pre-malignant or malignant cells. The location of the cells on the input slide is obtained from X-Y plane position coordinates outputted continually by the automated microscope. This positional information is outputted to printer or video display 17 along with diagnosis and patient identification information so that the classification can be reviewed by a pathologist.

In the preferred embodiment, the parallel structure of the neural network is emulated by execution with pipelined serial processing as performed by one of the commercially available neurocomputer accelerator boards. The operation of these neurocomputers is discussed in the Spectrum reference cited. The neural network preferably is a "Delta" processor, which is a commercially available neurocomputer of Science Applications International Corp. (SAIC) (see the Hecht-Nielsen reference above) that has demonstrated a sustained processing rate of $10^7$ interconnects/second in the feed-forward (i.e., non-training) mode. For a typical cervical smear containing 100,000 cells, 1–2% of the cells or approximately 1,500 images will require processing by classifier 15. As an example of the data rates which result, assume that following data compression an image 50 × 50 pixels is processed by classifier 15. The input layer for the neural network, therefore, consists of 2,500 processing elements or "neurons." The middle layer consists of approximately 25% of the input layer, or 625 neurons. (The number of output neurons is equal to the number of diagnostic categories of interest. This small number does not significantly affect this calculation.) The number of interconnects is thus (2500)(625) or approximately $1.5 \times 10^6$. At a processing rate of 10 interconnects/second, the processing by classifier 15 of the 1,500 images sent to it by classifier 14 will take less than four minutes. Currently available embodiments of classifier 14 operate at a rate of 50,000 cells/minute (refer to the Tien et al citation). With classifier 14 operating at a rate of 50,000 cells/minute, the four minutes consumed by classifier 15 is added to the two minutes used by classifier 14 for a total of six minutes to analyze the 100,000, cell images on the slide. As discussed above, an accurate manual cervical smear analysis takes approximately 15 minutes/slide. Prior art automated attempts using a non-neural network embodiment of classifier 15 require over one hour/slide. This example is not meant in any way to limit the actual configuration of the present invention, but rather to demonstrate that it is capable of achieving the object of processing cervical smears and other cytological samples within the time period required for commercially feasible operation.

In the preferred embodiment, primary classifier 14 is restricted to evaluation of the cellular nucleus while the secondary classifier 15 evaluates both the nucleus and its surrounding cytoplasm. The ratio between the nucleus and cytoplasm is an important indicator for pre-malignant and malignant cell classification. In an alternate embodiment, both classifier 14 and classifier 15 are limited to evaluation for the cellular nuclei.

Output information from the secondary classifier 15 is directed to an output monitor and printer 17, which may indicate a variety of information including, importantly, whether any cells appear to be malignant or pre-malignant, appear to require further examination, etc.

Figure 3:
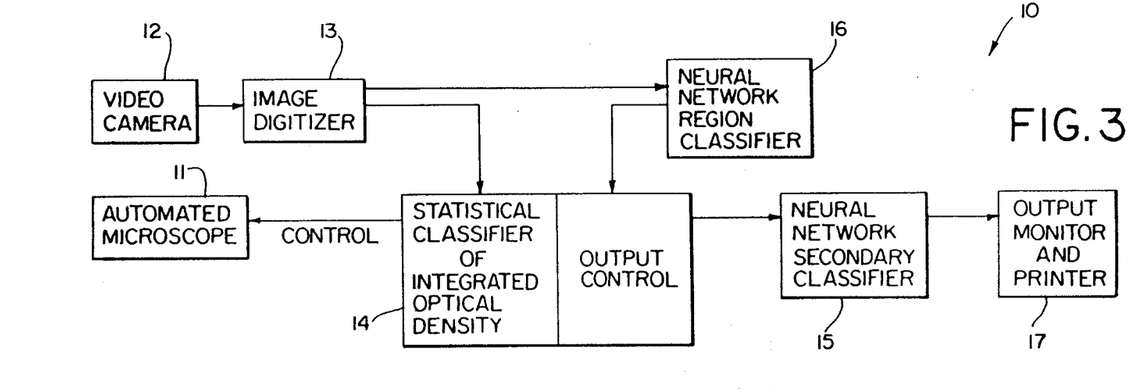
FIG. 3 is a block diagram of the alternate embodiment of the automated screening device in accordance with the present invention.

FIG. 3 illustrates an alternate embodiment in which an additional neural net classifier stage 16 is added to preprocess the slide for large areas of artifactual material, i.e., material other than single layer cells of interest. This includes clumps of cells, debris, mucus, leucocytes, etc. Positional information obtained in this pre-screen is stored for use by the remainder of the classification system. The information from classifier stage 16 is utilized to limit the processing required by classifier 15. Classifier stage 14 can ignore all material within the areas defined by the positional coordinates outputted by classifier 16. This will result in less information being sent for processing by classifier 15. A diagnosis is, therefore, made on the basis of classification of only those cells which lie outside of these areas. If an insufficient sample of cells lies outside of these areas for a valid diagnosis, this information will be outputted on 17 as an "insufficient cell sample."

Figure 4:
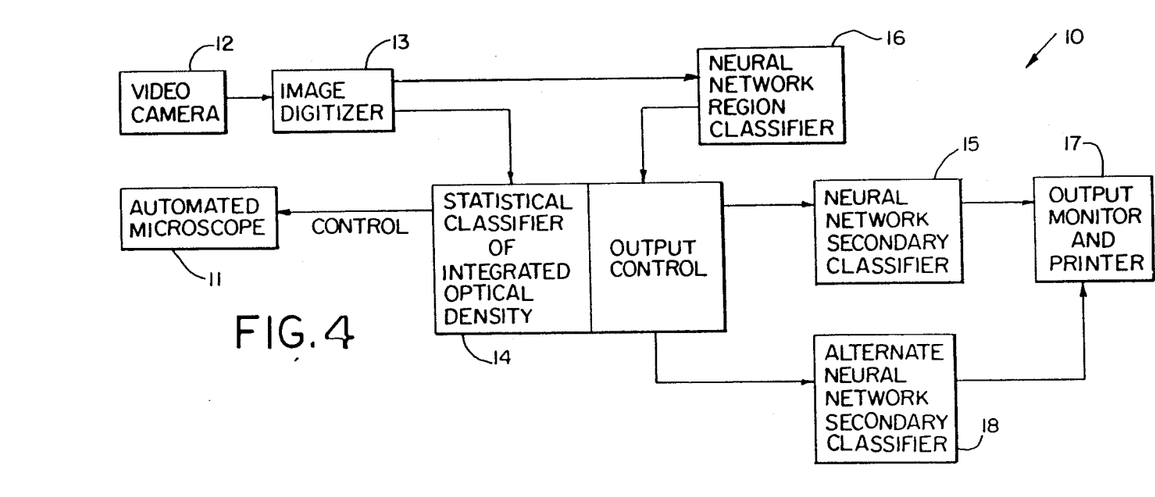
FIG. 4 is a block diagram of an alternate embodiment of the automated screening device in accordance with the present invention.

FIG. 4 illustrates an alternate embodiment in which the images within the areas identified by classifier 16 are not ignored but are instead processed by a separate classifier 18 which operates in parallel with classifier 15. The training of the neural net which composes classifier 18 is dedicated to the distinction of pre-malignant and malignant cells from said artifactual material.

Figures 5, 6:
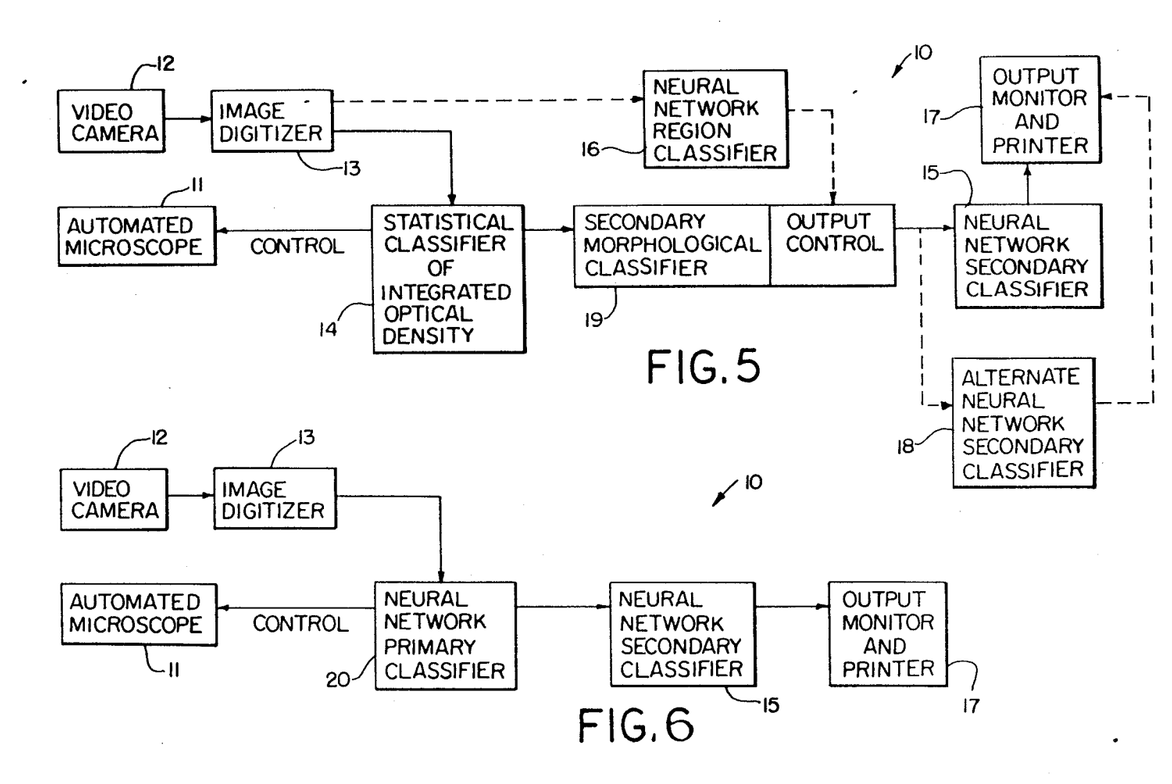
FIG. 5 is a block diagram of an alternate embodiment of the automated screening device in accordance with the present invention.
FIG. 6 is a block diagram of an alternate embodiment of the automated screening device in accordance with the present invention.

FIG. 5 illustrates an alternate embodiment wherein an additional non-neural net classification of nuclear morphological components, exclusive of integrated optical density, is placed between classifier 14 and classifier 15. This classification is performed by classifier 19.

FIG. 6 illustrates an alternate embodiment in which a commercially available SAIC neurocomputer is optimized for feed-forward processing 20. Through deletion of learning-mode capacity, all neurocomputer functions are dedicated to feedforward operation. Learning is completed on a separate unmodified neurocomputer which contains both the learning and feed-forward functions.

Following the completion of learning, the final interconnection weights are transferred to the optimized feedforward neurocomputer 20. Dedication of neurocomputer 20 to the feed-forward mode results in a sustained feed-forward operation rate of $10^8$ interconnects/second vs. $10^7$ interconnects/second for the non-optimized board as commercially supplied. The optimized feed-forward neural network 20 is utilized to perform the functions of classifiers 14 and 16 in FIGS. 1, 3, 4, and 5. By utilizing neural net classifier 20 to perform the function of statistical classifier 14, cells of interest which are not necessarily malignant cervical cells, and which do not therefore exceed the integrated optical density threshold of classifier 14, would nevertheless be detected. An example would be the detection of endometrial cells which, while not necessarily indicative of cervical malignancy, are indicative of uterine malignancy when found in the Pap smear of a post-menopausal patient.

As an example of the data rates that result from this embodiment in FIG. 6, assume outside slide dimensions of 15 mm $\times$ 45 mm or a total slide area of $675 \times 10^6$ micrometers$^2$. Neural net 20 processes a sliding window over this area for analysis. This window has dimensions of 20 micrometers $\times$ 20 micrometers or an area of 400 micrometers$^2$. There are, therefore, $1.5 \times 10^6$ of these windows on the 15 mm $\times$ 45 mm slide. For the primary classification function performed by neural net 20, a resolution of 1 micrometer/pixel is sufficient to detect those objects which must be sent to secondary neural network classifier 15 for further analysis. The input pattern for the image window analyzed by classifier 20 is therefore 20 $\times$ 20 pixels or 400 neurons to the input layer of neural net 20. The middle layer consists of approximately 25% of the input layer or 100 neurons. (As discussed above in the data rate calculation for classifier 15, the number of output layer neurons is small and does not significantly affect our results.) The number of interconnections in classifier 20 is thus approximately (400)(100) or $40 \times 10^3$. At a processing rate of $10^8$ interconnects/second, each image from the sliding window will take 400 microseconds for neural net 20 to classify. In a 15 mm $\times$ 45 mm slide, there are $1.5 \times 10^6$ of the 400 micrometer$^2$ windows which require classification by neural net 20. Total classification time for neural net 20 is therefore $(1.5 \times 10^6)(400 \times 10^{-6}) =$ 600 seconds or ten minutes. If this ten minutes is added to the approximately four minutes required for secondary neural net classifier 15, a total of 14 minutes/slide results. This example is not meant in any way to limit the actual configuration of the present invention, but rather to demonstrate that it is capable of achieving the object of processing cervical smears and other cytological samples within the time period required for commercially feasible operation.

Speed of processing data can be enhanced, too, by using parallel processing. For example, plural commercially available neurocomputers from SAIC can be coupled to effect parallel processing of data, thus increasing overall operational speed of the classifier using the same.

Figure 7:
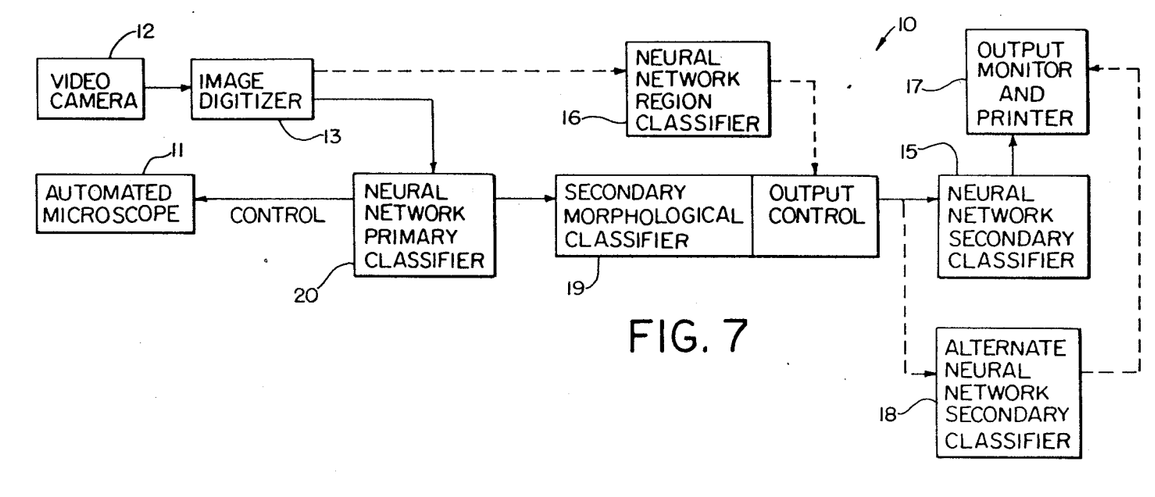
FIG. 7 is a block diagram of an alternate embodiment of the automated screening device in accordance with the present invention.

FIG. 7 illustrates an alternate embodiment in which neural net primary classifier 20 is utilized in conjunction with, rather than as a substitute for morphological classification and area classification. By dedication of classifier 20 to the detection of those few cell types which are of interest, but which cannot be detected by other means, the resolution required of classifier 20 is minimized.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. An automated cytological specimen classifier for classifying cells contained in a smear on a slide to identify cells that are likely to be malignant or pre-malignant, comprising:
    (a) microscope means for obtaining a vie of at least part of a cytological specimen including cells and other material located generally randomly on a slide in an arrangement which can include other than a single layer of cells,
    (b) camera means for creating an image of such view,
    (c) image digitizing means for producing a digital representation of such image,
    (d) a primary classifier means for detecting objects in a digital representation of a cytological specimen based on a detectable feature, said primary classifier means comprising a classifier means for detecting cells that are likely to be malignant or pre-malignant as well as other cells and material that initially appear to have characteristics of a malignant cell or a pre-malignant cell based on integrated optical density, and
    (e) a secondary classifier for distinguishing pre-malignant and malignant cells form other cells and material among the objects detected by the primary classifier, said secondary classifier means comprising a neural computer apparatus means for effecting such distinguishing as a function of training thereof.

2. The automated classifier of claim 1 wherein said primary classifier means comprises a statistical classifier.

3. The automated classifier of claim 1 wherein such cytological specimen includes overlapping cells.

4. The automated classifier of claim 1 wherein said secondary classifier means is operable to distinguish pre-malignant and malignant cells among overlapping arrangements of cells and other material.

5. The automated classifier of claim 1, wherein said camera means is positioned to create an image of a portion of such cytological specimen from such view.

6. The automated classifier of claim 1, said neural computer apparatus means comprising an electronic neural computer.

7. The automated classifier of claim 1 wherein the primary classifier means is restricted to evaluation of the cellular nucleus while the secondary classifier means evaluates both the cellular nucleus and its surrounding cytoplasm.

8. The automated classifier of claim 1 wherein both the primary classifier means and the secondary classifier means are restricted to evaluation of the cellular nucleus.

9. The automated classifier of claim 1 further comprising means for making an additional non-neural net classification of nuclear morphological components in addition to integrated optical density, said means being coupled between the primary classifier means and the secondary classifier means.

10. The automated classifier of claim 1, said microscope means comprising an automated microscope.

11. The automated classifier of claim 1, said camera means comprising a video camera.

12. The automated classifier of claim 1, said camera means comprising a charge coupled device.

13. The automated classifier of claim 1, said primary classifier means comprising means for detection of objects in such digital representation of a cytological specimen which has a feature that exceeds a threshold level.

14. The automated classifier of claim 1, said primary classifier means comprising means for detection of objects in such digital representation of a cytological specimen which has a feature that exceeds a threshold integrated optical density.

15. The automated classifier of claim 1, said primary classifier means comprising means for detection of objects in such digital representation of a cytological specimen based on morphological criteria.

16. The automated classifier of claim 1 further comprising a neural network pre-screening classifier means for recognition and classification of general areas within the digital representation of a specimen that contain material other than a cellular monolayer prior to primary classification by said primary classifier means.

17. The automated classifier of claim 16 wherein the output form the pre-screening classifier means is utilized to exclude such areas from further analysis.

18. The automated classifier of claim 16 wherein the output form the pre-screening classifier means is utilized to modify further analysis of images found within such areas.

19. A method of classifying cytological specimens, comprising using a primary classifier apparatus primarily classifying a specimen which is generally randomly arranged and can include other than in a single layer to determine locations of interest, and secondarily classifying such locations of interest using a neural network computer apparatus.

20. The method of claim 19, wherein said primarily classifying step comprises using a video camera or charge coupled device (CCD) to obtain images of the specimen, a digitizer to digitize such images and an integrated optical density detector.

21. The method of claim 19, wherein said primary classifying comprises using a neural network computer apparatus.

22. The method of claim 19, wherein said step of using a primary classifier apparatus primarily classifying a specimen comprises using a statistical classifier.

23. The method of claim 19, wherein said step of using a primary classifier apparatus primarily classifying a specimen comprises making a classification based on morphology.

24. The method of claim 19, wherein said step of using a primary classifier apparatus primarily classifying a specimen comprises making such primary classification based on integrated optical density.

25. The method of claim 19, further comprising training such neural network computer apparatus to identify cytological specimens of interest.

26. An automated cytological specimen classifier, comprising:
(a) microscope means for obtaining a view of at least part of a cytological specimen including cells and other material located generally randomly in an arrangement which can include other than a single layer of cells,
(b) camera means for creating an image of such view,
(c) image digitizing means for producing a digital representation of such image,
(d) primary classifier means for detecting objects in a digital representation of a cytological specimen based on a detectable feature, said primary classifier means comprising a classifier for detecting cells that are likely to be of a predetermined cell type as well as other cells and material that initially appear to have characteristics of such predetermined cell type, and
(e) secondary classifier means for distinguishing cells of such predetermined cell type from other cells and material among the objects detected by said primary classifier means, said secondary classifier means comprising a neural computer apparatus means for effecting such distinguishing as a function of training thereof.

27. The automated classifier of claim 16, wherein the primary classifier means is restricted to evaluation of the cellular nucleus while the secondary classifier means evaluates both the cellular nucleus and its surrounding cytoplasm.

28. The automated classifier of claim 26 wherein both the primary classifier means and the secondary classifier means are restricted to evaluation of the cellular nucleus.

29. The automated classifier of claim 26, further comprising means for making an additional non-neural net classification of nuclear morphological components, said means being coupled between the primary classifier means and said secondary classifier means.

30. The automated classifier of claim 26, said microscope means comprising an automated microscope.

31. The automated classifier of claim 16, said camera means comprising a video camera.

32. The automated classifier of claim 26, said camera means comprising a charge coupled device.

33. The automated classifier of claim 26, said primary classifier means comprising means for detection of objects in such digital representation of a cytological specimen which have a feature that exceeds a threshold level.

34. The automated classifier of claim 26, said primary classifier means comprising means for detection of objects in such digital representation of a cytological specimen which has a feature that exceeds a threshold integrated optical density.

35. The automated classifier of claim 26, said primary classifier means comprising means for detection of objects in such digital representation of a cytological specimen based on morphological criteria.

36. The automated classifier of claim 26, wherein said camera means is positioned to create an image of a portion of such cytological specimen from such view.

37. The automated classifier of claim 26, said neural computer apparatus means comprising an electronic neural computer.

38. The automated classifier of claim 16 wherein primary classifier means comprises a statistical classifier.

39. The automated classifier of claim 16 wherein such cytological specimen includes overlapping cells.

40. The automated classifier of claim 16 wherein said secondary classifier means is operable to distinguish cells of such predetermined cell type among overlapping arrangements of cells and other materials.

41. The automated classifier of claim 26 further comprising a neural network pre-screening classifier means for identifying general areas within the digital representation of a specimen that contain material other than a cellular monolayer prior to primary classification.

42. The automated classifier of claim 41 wherein the output from the pre-screening classifier is utilized to exclude such identified areas from further analysis.

43. The automated classifier of claim 41 wherein the output from the pre-screening classifier means is utilized to modify further analysis of images found within the areas of the specimen identified by said pre-screening classifier means.

* * * * *

UNITED STATES PATENT AND TRADEMARK OFFICE
CERTIFICATE OF CORRECTION

PATENT NO. : 4,965,725

DATED : October 23, 1990

INVENTOR(S) : Mark R. Rutenberg

It is certified that error appears in the above-identified patent and that said Letters Patent is hereby corrected as shown below:

On the title page the assignee "Nueromedical Systems, Inc." should be rewritten as --Neuromedical Systems, Inc.--.
Column 4, line 46, "196" should be rewritten as --1969--.
Column 8, line 44, "vie" should read --view--; line 63, "form" should read --from--.
Column 9, line 41, "has" should read --have--; line 58, "form" should read --from--; line 61, "form" should read --from--.
Column 10, line 51, claim reference numeral "16" should read --26--; line 67, claim reference numeral "16" should read --26--.
Column 12, lines 1, 4 and 6, each occurrence of claim reference numeral "16" should read --26--.

Signed and Sealed this

Eleventh Day of August, 1992

Attest:

DOUGLAS B. COMER

*Attesting Officer*   *Acting Commissioner of Patents and Trademarks*

REEXAMINATION CERTIFICATE (2866th)
United States Patent [19]
Rutenberg

[11] B1 4,965,725

[45] Certificate Issued May 7, 1996

[54] NEURAL NETWORK BASED AUTOMATED CYTOLOGICAL SPECIMEN CLASSIFICATION SYSTEM AND METHOD

[75] Inventor: Mark R. Rutenberg, Monsey, N.Y.

[73] Assignee: Neuromedical Systems, Inc., Monsey, N.Y.

Reexamination Request:
No. 90/003,818, May 2, 1995

Reexamination Certificate for:
Patent No.: 4,965,725
Issued: Oct. 23, 1990
Appl. No.: 179,060
Filed: Apr. 8, 1988

[51] Int. Cl.⁶ .............. G06F 15/18; G06K 9/62
[52] U.S. Cl. .............. 364/413.1; 395/21; 395/22; 382/133; 382/156; 382/159

[56] References Cited

U.S. PATENT DOCUMENTS 3,333,248  7/1967  Greenberg et al. .
3,824,393  7/1974  Brain .

OTHER PUBLICATIONS

Publication entitled *"The Second International Conference on Artificial Intelligence Systems (EXPERT SYSTEMS) as Diagnostic Consultants for the Cytologic and Histologic Diagnosis of Cancer"*, Abstracts, (The International Academy of Cytology, American Society of Cytology, The Tutorials of Cytology at the University of Chicago, Mar. 13–15, 1988) (Held at the Drake Hotel Chicago, Il).

*Primary Examiner*—Ruth S. Smith

[57] ABSTRACT

An automated screening system and method for cytological specimen classification in which a neural network is utilized in performance of the classification function. Also included is an automated microscope and associated image processing circuitry.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–43 is confirmed.

* * * * *